(12) United States Patent  
Kudo et al.

(10) Patent No.: US 7,857,797 B2  
(45) Date of Patent: Dec. 28, 2010

(54) SANITARY NAPKIN HAVING A LOW STIFFNESS REGION AND INCISIONS

(75) Inventors: Jun Kudo, Kagawa (JP); Takuya Miyama, Kagawa (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 214 days.

(21) Appl. No.: 11/206,008

(22) Filed: Aug. 16, 2005

(65) Prior Publication Data  
US 2006/0058761 A1 Mar. 16, 2006

(30) Foreign Application Priority Data  
Sep. 14, 2004 (JP) .............................. 2004-266176

(51) Int. Cl.  
A61F 13/15 (2006.01)  
A61F 13/20 (2006.01)

(52) U.S. Cl. .................. 604/385.01; 604/383; 604/358; 604/378; 604/380; 604/385.16; 604/385.23

(58) Field of Classification Search .................. 604/383, 604/385.01, 358, 378, 380, 385.16, 385.23  
See application file for complete search history.

(56) References Cited

U.S. PATENT DOCUMENTS

| | | | | |
|---|---|---|---|---|
| 3,889,679 A * | 6/1975 | Taylor | ............ | 604/378 |
| 3,927,673 A * | 12/1975 | Taylor | ............ | 604/366 |
| 5,387,206 A * | 2/1995 | Valentine et al. | ............ | 604/358 |
| 5,536,555 A * | 7/1996 | Zelazoski et al. | ............ | 428/138 |
| 5,804,021 A * | 9/1998 | Abuto et al. | ............ | 156/252 |
| 5,941,863 A | 8/1999 | Guidotti et al. | | |
| 5,961,505 A * | 10/1999 | Coe et al. | ............ | 604/378 |
| 6,312,416 B1 * | 11/2001 | Brisebois et al. | ....... | 604/385.01 |
| 6,410,820 B1 * | 6/2002 | McFall et al. | ............ | 604/369 |
| 6,417,427 B1 * | 7/2002 | Roxendal et al. | ............ | 604/378 |
| 6,503,233 B1 * | 1/2003 | Chen et al. | ............ | 604/385.01 |
| 6,506,961 B1 * | 1/2003 | Levy | ............ | 604/380 |
| 7,612,248 B2 * | 11/2009 | Burton et al. | ............ | 602/58 |
| 7,628,777 B2 * | 12/2009 | Kondo et al. | ......... | 604/385.101 |
| 7,632,979 B2 * | 12/2009 | Fujii et al. | ............ | 604/378 |
| 7,696,400 B2 * | 4/2010 | Sigurjonsson et al. | ......... | 602/56 |
| 7,795,492 B2 * | 9/2010 | Vartiainen | ............ | 604/378 |
| 2001/0039406 A1 * | 11/2001 | Hamajima et al. | ............ | 604/367 |
| 2002/0004654 A1 * | 1/2002 | Daniels et al. | ............ | 604/380 |
| 2003/0187418 A1 * | 10/2003 | Kudo et al. | ............ | 604/380 |

FOREIGN PATENT DOCUMENTS

EP 0293208 A1 * 11/1988

(Continued)

Primary Examiner—Tatyana Zalukaeva  
Assistant Examiner—Ginger T Chapman  
(74) Attorney, Agent, or Firm—Morrison & Foerster LLP

(57) ABSTRACT

Disclosed is a sanitary napkin including a liquid absorbent layer and a liquid-permeable topsheet covering a body surface of the liquid absorbent layer. The topsheet is joined to the liquid absorbent layer in a specific pattern. The pattern includes longitudinal join lines which extend longitudinally and are laterally spaced from each other and a connecting join line which connects the longitudinal join lines. The liquid absorbent layer has a low stiffness portion in a region enclosed by the longitudinal join lines and the connecting join line. The liquid absorbent layer has a lower stiffness in the low stiffness portion than in portions outside the longitudinal join lines.

13 Claims, 14 Drawing Sheets

FOREIGN PATENT DOCUMENTS

| | | |
|---|---|---|
| JP | 4-51930 U | 4/1992 |
| JP | 10-511582 | 11/1998 |
| JP | 10-328233 | 12/1998 |
| JP | 11-070141 | 3/1999 |
| JP | 2002-035036 A | 2/2002 |
| JP | 2003-310659 | 11/2003 |
| JP | 2004-105696 | 4/2004 |
| WO | WO-9620670 | 7/1996 |

\* cited by examiner

SANITARY NAPKIN HAVING A LOW STIFFNESS REGION AND INCISIONS

BACKGROUND OF THE INVENTION

1. Field of the Invention

The present invention relates to a sanitary napkin which is adapted to deform in accordance with the wearer's body shape, comfortable to wear and less noticeable from the outside during wear.

2. Description of the Related Art

Sanitary napkins (feminine hygiene product intended to be applied to the vaginal opening of a menstruating woman) are typically constructed to include a liquid absorbent layer containing pulp, superabsorbent polymer (SAP), etc. and a liquid-permeable topsheet covering a body surface of the liquid absorbent layer.

When put on with the sanitary napkin applied to the vaginal opening, shorts exert an elastic lifting force in the crotch region. The sanitary napkin, which is intended to be in close contact with the vaginal opening, is preferably deformed by the lifting force in accordance with the shape of the woman's crotch region. However, the liquid absorbent layer, which is mainly of pulp and thick, hinders the sanitary napkin from deforming in accordance with the shape of the crotch region and coming into close contact with the vaginal opening.

When the sanitary napkin is worn in the crotch region, the rear end of the sanitary napkin will be positioned slightly posterior to the anus and face the lower part of the buttocks. Particularly when the sanitary napkin is elongated to prevent leakage of menstrual blood toward the buttocks, the rear end of the sanitary napkin will be positioned near the coccyx. When wearing the shorts with the rear end of the sanitary napkin positioned on the lower part of the buttocks, accordingly, if the liquid absorbent layer is thick and cannot easily be deformed by the lifting force of the shorts in accordance with the cleft of the buttocks, the rear end of the sanitary napkin will be noticeable from the outside when wearing tight-fitting pants or the like.

The following patent documents disclose conventional sanitary napkins with a liquid absorbent layer adapted to deform in accordance with the crotch region or the cleft of the buttocks.

Firstly, Japanese Unexamined Patent Application Publication No. H10-328233 discloses an elongated sanitary napkin whose rear part has a liquid absorbent layer with longitudinally extending compressed grooves. When the shorts exert a lifting force on the compressed grooves, the liquid absorbent layer tends to deform at the compressed grooves in accordance with the cleft of the buttocks.

Secondly, Japanese Unexamined Utility-Model Application Publication No. H04-51930 discloses a sanitary napkin in which a liquid absorbent layer is made more deformable by forming a plurality of slit-like incisions in the liquid absorbent layer. As a result, the sanitary napkin tends to deform in accordance with the wearer's body shape and hardly feels rough.

Thirdly, Japanese Unexamined Patent Application Publication No. 2002-35036 discloses a sanitary napkin in which a liquid absorbent layer is made more flexible by forming a number of through-holes in the liquid absorbent layer.

In the sanitary napkin disclosed in Japanese Unexamined Patent Application Publication No. H10-328233, however, since the density of the liquid absorbent layer is increased at the compressed grooves, a wearer tends to feel uncomfortable when the compressed grooves are pressed against the cleft of the buttocks.

In the sanitary napkins disclosed in Japanese Unexamined Utility-Model Application Publication No. H04-51930 and Japanese Unexamined Patent Application Publication No. 2002-35036, on the other hand, since the liquid absorbent layer has weak tensile strength as a whole due to the slit-like incisions or the through-holes distributed over the liquid absorbent layer, the incisions or the through-holes tend to cause a breakage in the liquid absorbent layer when a wearer moves her body with the sanitary napkin worn in the crotch region.

Moreover, since all the liquid absorbent layers disclosed in the foregoing patent documents are made of a pulp deposition and thick, the sanitary napkins tend to be noticeable from the outside when wearing tight-fitting pants or the like, regardless of whether the liquid absorbent layer can deform in accordance with the crotch region or the cleft of the buttocks.

SUMMARY OF THE INVENTION

The present invention has been developed to solve the problems in the prior art set forth above and has an object to provide a sanitary napkin which is adapted to deform in accordance with the wearer's body shape, hardly causes a breakage in a liquid absorbent layer, and is less noticeable from the outside when wearing pants or the like.

According to the present invention, there is provided a sanitary napkin comprising a liquid absorbent layer and a liquid-permeable topsheet covering a body surface of the liquid absorbent layer, the topsheet being joined to the liquid absorbent layer in a specific pattern, the pattern including longitudinal join lines which extend longitudinally and are laterally spaced from each other and a connecting join line which connects the longitudinal join lines, the liquid absorbent layer having a low stiffness portion in a region enclosed by the longitudinal join lines and the connecting join line, the liquid absorbent layer having a lower stiffness in the low stiffness portion than in portions outside the longitudinal join lines.

Since the liquid absorbent layer has the low stiffness portion between the longitudinal join lines, when shorts exert a lifting force, the sanitary napkin of the present invention can deform between the longitudinal join lines in accordance with the crotch region or the cleft of the buttocks. This enables the body surface of the sanitary napkin to have a close fit with the vaginal opening and makes the sanitary napkin less noticeable from the outside when wearing tight-fitting pants or the like. Here, since the topsheet extends between the right and left longitudinal join lines, the low stiffness portion of the liquid absorbent layer is reinforced and prevented from being stretched laterally by an external force.

According to one embodiment of the present invention, the liquid absorbent layer may have a plurality of incisions in the low stiffness portion. The incisions may pierce (or run through) the liquid absorbent layer. Alternatively, the incisions may terminate midway through the liquid absorbent layer in the thickness direction. Preferably, each incision extends straight and crosses another incision so that the liquid absorbent layer may be flexible in all directions.

Alternatively, the low stiffness portion may be formed by decreasing at least either of unit weight and density of the liquid absorbent layer. This may be achieved by locally stretching the liquid absorbent layer.

According to one embodiment of the present invention, a fibrous layer having a lower density than the liquid absorbent layer may be interposed between the low stiffness portion and the topsheet. With such a low density fibrous layer on the low stiffness portion, the sanitary napkin may be made soft to the touch without impairing the flexibility of the liquid absorbent layer within the low stiffness portion. Moreover, the liquid absorption capacity may be increased by combining the fibrous layer with the liquid absorbent layer.

Preferably, the liquid absorbent layer may be an air-laid pulp. Alternatively, the liquid absorbent layer may be formed by compressing a fiber deposition including pulp fibers. With this construction, the liquid absorbent layer may be made flexible as a whole. In addition, the whole liquid absorbent layer may be made so thin that the sanitary napkin can be less noticeable from the outside when wearing pants or the like.

BRIEF DESCRIPTION OF THE DRAWINGS

The present invention will be understood more fully from the detailed description given hereinafter and from the accompanying drawings of the preferred embodiments of the present invention, which, however, should not be taken to limit the invention, but are for explanation and understanding only.

In the drawings.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscuring of the present invention.

Figure 1:
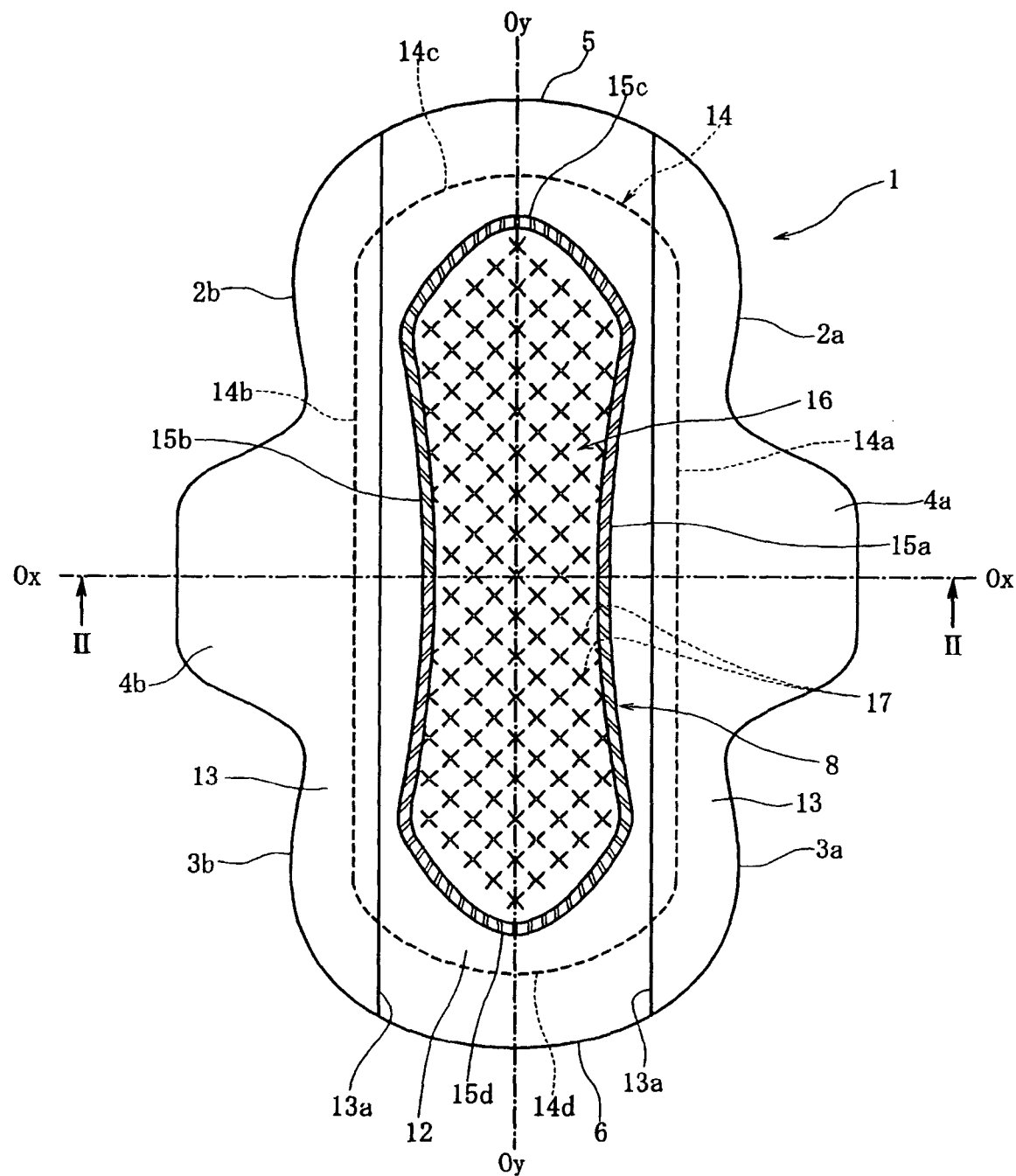
FIG. 1 is a plan view of a sanitary napkin according to a first embodiment of the present invention.
Figure 2:
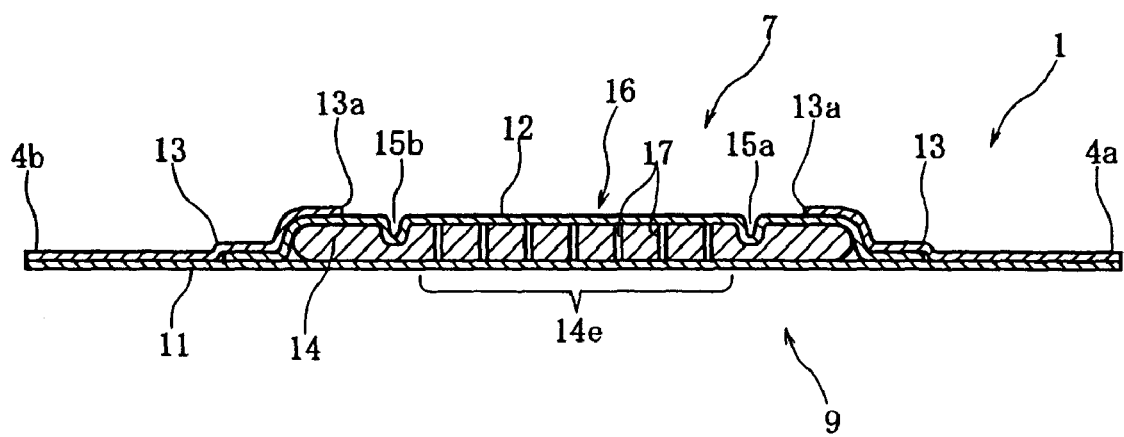
FIG. 2 is a sectional view of the sanitary napkin of FIG. 1 taken along line II-II.

FIG. 1 is a plan view showing a body surface of a sanitary napkin 1 according to a first embodiment of the present invention, and FIG. 2 is a sectional view taken along line II-II of FIG. 1.

As shown in the plan view of FIG. 1, the sanitary napkin 1 has a front right side edge 2a, a front left side edge 2b, a rear right side edge 3a, a rear left side edge 3b. On the right side, a right fold-back flap 4a projects laterally from between the front right side edge 2a and the rear right side edge 3a, and on the left side, a left fold-back flap 4b projects laterally from between the front left side edge 2b and the rear left side edge 3b. Moreover, the sanitary napkin 1 has a front edge 5 on the front side and a rear edge 6 on the rear side.

FIG. 1 shows a longitudinal centerline Oy, which laterally bisects the sanitary napkin 1, and a lateral reference line Ox, on which the distance between right and left longitudinal join lines 15a, 15b is reduced to a minimum. The sanitary napkin 1 is intended to be brought into contact with the center of the vaginal opening near the intersection of the longitudinal centerline Oy and the lateral reference line Ox. In the embodiment shown in FIG. 1, the lateral reference line Ox longitudinally bisects the right and left fold-back flaps 4a, 4b and the sanitary napkin 1 is longitudinally symmetrical about the lateral reference line Ox.

As shown in FIG. 2, the sanitary napkin 1 has a garment surface 9 intended to face the inner side of shorts and a body surface 7 intended to face the body of a wearer.

On the side of the garment surface 9, a liquid-blocking backsheet 11 is exposed externally. The backsheet 11 may be of the same shape and size as the sanitary napkin 1. On the side of the body surface 7, a liquid-permeable topsheet 12 is disposed with laterally opposite sides covered with right and left liquid-blocking side sheets 13, 13. The regions defined between inner edges 13a, 13a of the right and left liquid-blocking side sheets 13, 13 is a liquid absorbing region 8 where the liquid-permeable topsheet 12 is exposed externally.

Between the backsheet 11 and the topsheet 12, there is provided a liquid absorbent layer 14. As shown in FIG. 1, the liquid absorbent layer 14 has right and left longitudinally-extending side edges 14a, 14b, a front edge 14c on the front side, and a rear edge 14d on the rear side. Here, the side sheets 13, 13 overlap with the liquid absorbent layer 14 with the inner edges 13a, 13a located slightly inside the right and left side edges 14a, 14b (or located closer to the longitudinal centerline Oy than the right and left side edges 14a, 14b).

In the liquid absorbing region 8, there is formed a specific pattern of join lines where the topsheet 12 and the liquid absorbent layer 14 are joined together by fusion-bonding them under pressure. The pattern includes the right longitudinal join line 15a, which extends longitudinally on the right side of the longitudinal centerline Oy, the left longitudinal join line 15b, which extends longitudinally on the left side of the longitudinal centerline Oy, a front connecting join line 15c, which extends laterally on the front side, and a rear connecting join line 15d, which extends laterally on the rear side. As described hereinabove, the distance between the right and left longitudinal join lines 15a, 15b is reduced to a minimum on the lateral reference line Ox.

The join lines 15a, 15b, 15c and 15d are connected together to define an elongated enclosure 16 in the body surface 7 of the sanitary napkin 1.

The individual join lines 15a, 15b, 15c and 15d are formed by pressing the topsheet 12 and the liquid absorbent layer 14 under heat toward the side of the garment surface 9, whereby thermoplastic fibers contained in the topsheet 12 may be fusion-bonded for joining and fixing the topsheet 12 to the liquid absorbent layer 14. In the individual join lines 15a, 15b, 15c and 15d, high-density parts, where the topsheet 12 and the liquid absorbent layer 14 are compressed with high density, may alternate with medium-density parts, where the topsheet 12 and the liquid absorbent layer 14 are also compressed but has a lower density than the high-density parts. Here, the individual join lines 15a, 15b, 15c and 15d extend as a groove formed in the body surface 7, as shown in FIG. 2.

The liquid absorbent layer 14 is an air-laid pulp or air-laid nonwoven fabric which is made of pulp fibers alone or in combination with thermoplastic synthetic resin fibers such as polyethylene (PE), polypropylene (PP), polyethylene terephthalate (PET), etc. After deposited by an air-laid process, the fibers may be pressed between pressing rolls into the form of a sheet and bonded together through a binder such as an acrylic binder. The liquid absorbent layer 14 may further contain superabsorbent polymer (SAP). Alternatively, the fibers deposited by an air-laid process may be bonded together by fusion of the thermoplastic synthetic fibers, without adding the binder.

The liquid absorbent layer 14 may have a unit weight in the range of 70 to 300 g/m$^2$ and contain 70 to 100% pulp by weight and 0 to 30% synthetic resin fibers by weight. The liquid absorbent layer 14 may have a density in the range of 0.05 to 0.2 g/cm$^3$. If desired, the liquid absorbent layer 14 may further contain 0 to 20% SAP by weight.

In the enclosure 16, the liquid absorbent layer (air-laid pulp or air-laid nonwoven fabric) 14 has a number of incisions 17. Term "incision" as used herein refers to a hollow formed by cutting constituent fibers of the liquid absorbent layer and does not refer to a hollow formed by embossing (or locally compressing) the liquid absorbent layer. The incisions 17 may be formed by cutting fibers from one side to terminate midway through the liquid absorbent layer 14 in the thickness direction or pierce the liquid absorbent layer 14 from one side to the other. In the embodiment shown in FIG. 1, the incisions 17 are distributed over the enclosure 16, so that the liquid absorbent layer 14 in the enclosure 16 functions as a low stiffness portion 14e.

In the embodiment shown in FIG. 1, each incision 17 extends like a short straight line (or slit) and crosses another incision 17, and pairs of crossing incisions 17 are regularly arranged. The incisions 17, each inclined at an angle of 45 degrees to both the longitudinal centerline Oy and the lateral reference line Ox, cross each other at an angle of about 90 degrees. In the embodiment shown in FIG. 1, the incisions 17 are not formed outside the enclosure 16.

In the low stiffness portion 14e, the liquid absorbent layer 14 has a thickness of 0.5 to 10 mm, preferably 1 to 7 mm, more preferably 1.5 to 5 mm. Furthermore, at least either of the length ratio of the low stiffness portion 14e to the liquid absorbent layer 14 and the area ratio of the low stiffness portion 14e to the liquid absorbent layer 14 is preferably equal to or greater than 30%. When the low stiffness portion 14e has a thickness within the above range and occupies at least 30% of the length or area of the liquid absorbent layer 14, the low stiffness portion 14e can easily be deformed in accordance with the shape of the crotch region or the cleft of the buttocks.

It should be noted that unless otherwise stated, low stiffness portions according to other embodiments have the same preferred ranges with respect to the thickness and so on as the low stiffness portion 14e according to the first embodiment.

The liquid-permeable topsheet 12 may be a liquid-permeable nonwoven fabric, an apertured nonwoven fabric with a large number of liquid passage apertures, an apertured resin film with a large number of liquid passage apertures or a combination thereof. For example, the topsheet 12 may be a through-air bonded nonwoven fabric in which sheath/core bicomponent synthetic fibers with polyethylene terephthalate (PET) core and polyethylene (PE) sheath are fusion-bonded together by hot air. The through-air bonded nonwoven fabric may have a basis weight of about 15 to 35 g/m$^2$.

The liquid-blocking backsheet 11 may be made of low-density polyethylene (LDPE) and preferably has a basis weight of about 15 to 35 g/m$^2$. The side sheet 13 may be a liquid-blocking or water-repellent nonwoven fabric or resin film. For example, a through-air bonded or spunbonded nonwoven fabric may be employed.

When putting on the sanitary napkin 1, the garment surface 9 is adhered to the inner side of the crotch region of the shorts through a pressure-sensitive adhesive layer (not shown) on the backsheet 11 so that the body surface 7 can face the vaginal opening near the intersection of the longitudinal centerline Oy and the lateral reference line Ox. Then, the right and left fold-back flaps 4a, 4b are folded back to cover the side edges of the crotch region of the shorts and adhered to the outer side of the shorts through pressure-sensitive adhesive layers (not shown) on the garment surfaces of the fold-back flap 4a, 4b.

When wearing the shorts, a lifting force acts in the crotch region. Particularly when the shorts have a longitudinally extending elastic string or the like centrally of the back body, the elastic string exerts a lifting force to press the sanitary napkin 1 against the wearer's body along the longitudinal centerline Oy.

The enclosure 16 is elongated longitudinally of the sanitary napkin 1 along the longitudinal centerline Oy and the liquid absorbent layer 14 has the low stiffness portion 14e within the enclosure 16. Therefore, the low stiffness portion 14e can deform to bulge along the longitudinal centerline Oy. More specifically, the low stiffness portion 14e can deform to have a reversed V-shaped cross-section with its peak at the longitudinal centerline Oy, as taken along a plane perpendicular to the longitudinal centerline Oy. As a result, the body surface of the enclosure 16 can easily be brought into close contact with the vaginal opening.

Here, the thickness of the liquid absorbent layer 14 is as thin as 0.5 to 10 mm, preferably 1 to 7 mm, more preferably 1.5 to 5 mm, and furthermore, the rear part of the sanitary napkin 1 can easily be deformed by a lifting force of the shorts to fit in the cleft of the buttocks along with the low stiffness portion 14e. As a result, the sanitary napkin 1 is less noticeable from the outside when wearing tight-fitting pants or the like with the rear edge 6 of the sanitary napkin 1 positioned on the lower part of the buttocks.

Menstrual blood that is discharged from the vaginal opening can be applied mainly to the enclosure 16. The menstrual blood passes through the topsheet 12 and is then absorbed mainly by the low stiffness portion 14e of the liquid absorbent layer 14. The menstrual blood tends to diffuse in all directions in the low stiffness portion 14e, but can be blocked by the individual join lines 15a, 15b, 15c, 15d so as not to diffuse outside the enclosure 16.

The low stiffness portion 14e has a number of the incisions 17. However, because the liquid absorbent layer 14 is an air-laid pulp or air-laid nonwoven fabric, formation of many incisions 17 doesn't cause an extreme reduction in lateral tensile strength of the liquid absorbent layer 14.

Furthermore, the topsheet 12, which covers the body surface of the low stiffness portion 14e, is joined to the liquid absorbent layer 14 along the right and left longitudinal join lines 15a, 15b, and the right and left longitudinal join lines 15a, 15b are connected to each other through the front and rear connecting join lines 15c, 15d. Therefore, when the low stiffness portion 14e is subjected to a force which acts to separate the right and left longitudinal join lines 15a, 15b from each other, the topsheet 12 functions to prevent lateral stretch of the low stiffness portion 14e.

Accordingly, the individual incisions 17 are prevented from laterally spreading under lateral tensile force, so that the low stiffness portion 14e is prevented from causing breakage from the incisions 17 and further from decreasing in liquid absorption capacity due to spreading of the incisions 17.

In the following, the detailed description of the portions having the same construction as those of the first embodiment will be omitted by designating them by the common reference numerals.

FIGS. 3 to 9 illustrate modifications of the first embodiment.

Figure 3:
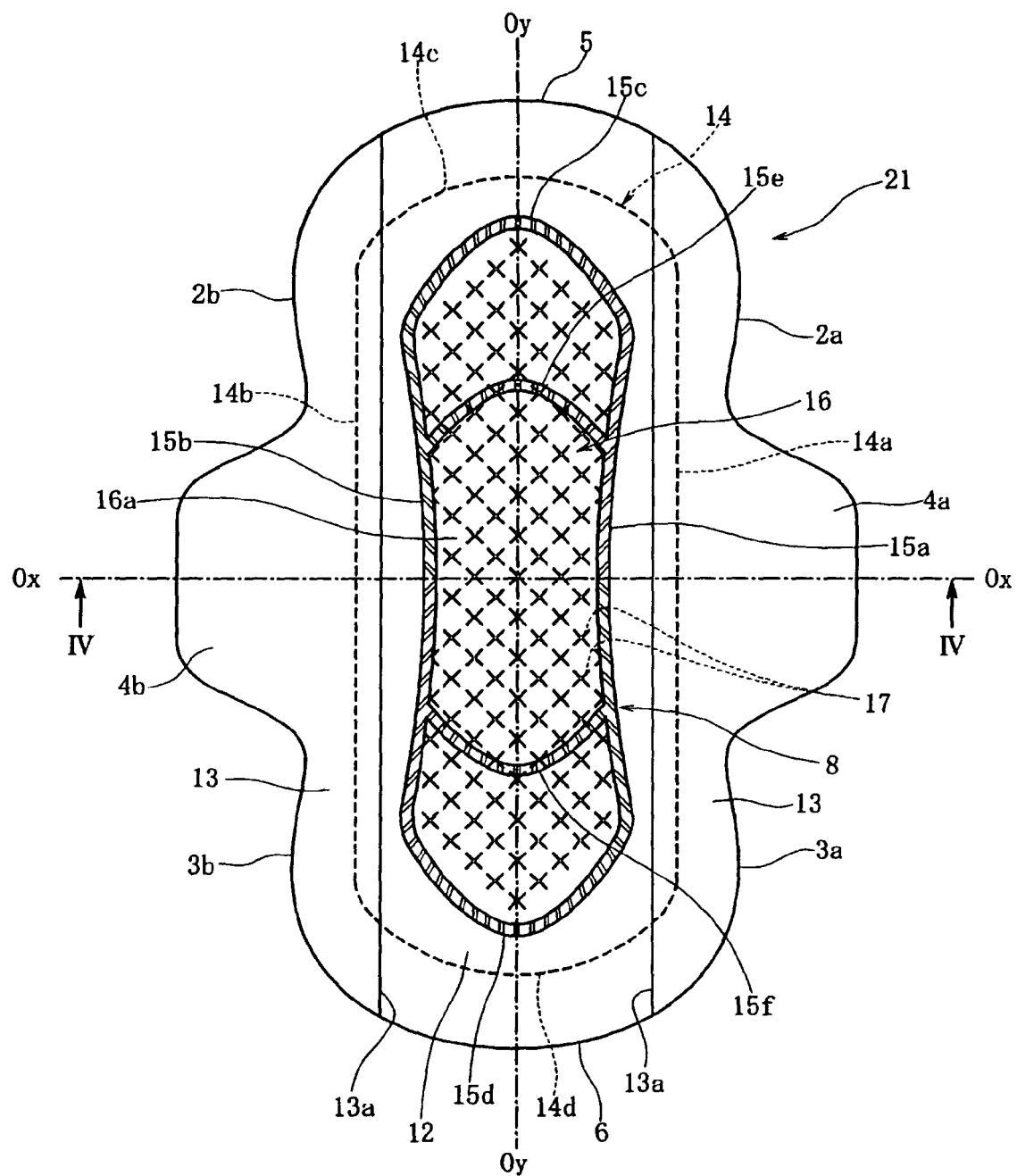
FIG. 3 is a plan view showing a modification of the first embodiment.
Figure 4:
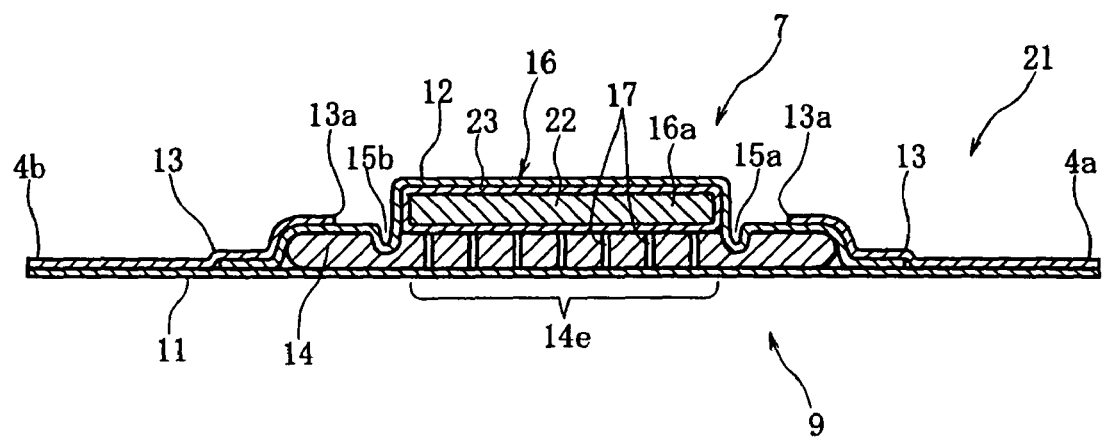
FIG. 4 is a sectional view of the sanitary napkin of FIG. 3 taken along line IV-IV.

FIG. 3 is a plan view of a sanitary napkin 21 as a modification of the first embodiment and FIG. 4 is a transverse sectional view taken along line IV-IV of FIG. 3.

The sanitary napkin 21 shown in FIG. 3 has the same contour as the sanitary napkin 1 shown in FIG. 1. Also in the sanitary napkin 21, the enclosure 16 is defined by the right longitudinal join line 15a, the left longitudinal join line 15b, the front connecting join line 15c and the rear connecting join line 15d, and in the enclosure 16, the liquid absorbent layer 14 has the low stiffness portion 14e with a number of the incisions 17.

In the enclosure 16, furthermore, there are formed front and rear internal connecting join lines 15e, 15f. The front and rear internal connecting join lines 15e, 15f connect the right and left longitudinal join lines 15a, 15b.

As with the sanitary napkin 1, the liquid absorbent layer 14 is an air-laid pulp or air-laid nonwoven fabric. In a central region 16a enclosed by the right longitudinal join line 15a, the left longitudinal join line 15b, the front internal connecting join line 15e and the rear internal connecting join line 15f, furthermore, there is disposed an absorbent fibrous layer 22 between the low stiffness portion 14e of the liquid absorbent layer 14 and the topsheet 12, as shown in FIG. 4.

The absorbent fibrous layer 22 has a lower density than the liquid absorbent layer 14 but is capable of absorbing and retaining liquid. For example, the absorbent fibrous layer 22 may be made of pulp fibers or a mixture of pulp fibers and superabsorbent polymer (SAP). It may also contain synthetic resin fibers in addition to natural fibers such as pulp fibers. In the absorbent fibrous layer 22, fibers are not bonded together either through a binder or by fusion, so that the absorbent fibrous layer 22 has a lower bending stiffness than the liquid absorbent layer 14. The absorbent fibrous layer 22 may have a density in the range of 0.02 to 0.15 g/cm$^3$ and a unit weight in the range of about 200 to 800 g/m$^2$.

The absorbent fibrous layer 22 may be disposed between the liquid absorbent layer 14 and the topsheet 12 while being wrapped in a hydrophilic paper material 23 such as tissue.

In the sanitary napkin 21, since the low-density absorbent fibrous layer 22 is laid on the low stiffness portion 14e with a number of the incisions 17, a sufficient liquid absorption capacity can be ensured by the low stiffness portion 14e with the incisions 17 and the absorbent fibrous layer 22. Moreover, the low-density absorbent fibrous layer 22, which is flexible, can easily follow the deformation of the low stiffness portion 14e to have a reversed V-shaped cross-section.

In the sanitary napkin 21, the central region 16a, which is designed to face the vaginal opening, has a sufficient liquid absorption capacity due to the presence of the liquid absorbent layer 14 and the absorbent fibrous layer 22. In a rear region 16b enclosed by the right longitudinal join line 15a, the left longitudinal join line 15b, the rear connecting join line 15d and the rear internal connecting join line 15f, however, there is provided only the low stiffness portion 14e of the liquid absorbent layer 14. That is, the rear region 16b does not include the absorbent fibrous layer 22. Hence, the rear region 16b becomes thin and easy to deform so that this part can easily fit in the cleft of the buttocks near and behind the anus, which makes the sanitary napkin 21 less noticeable from the outside when wearing tight-fitting pants or the like.

Here, it is preferred that at least in the rear part of the sanitary napkin, the low stiffness portion is formed in a region which is enclosed at least on three sides by the right and left longitudinal join lines and one connecting join line connecting the longitudinal join lines.

Figure 5:
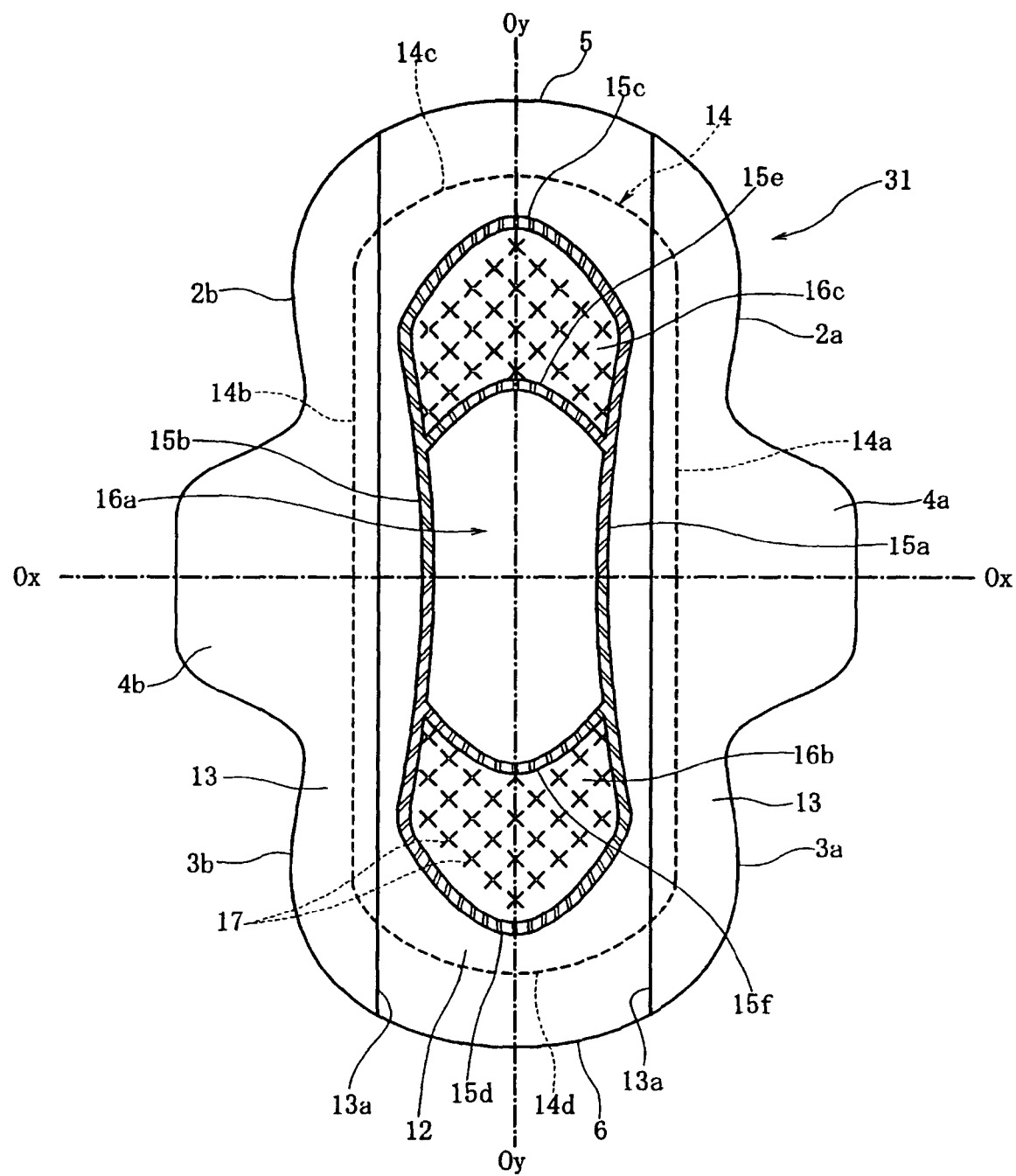
FIG. 5 is a plan view showing a modification of the first embodiment.
Figure 6:
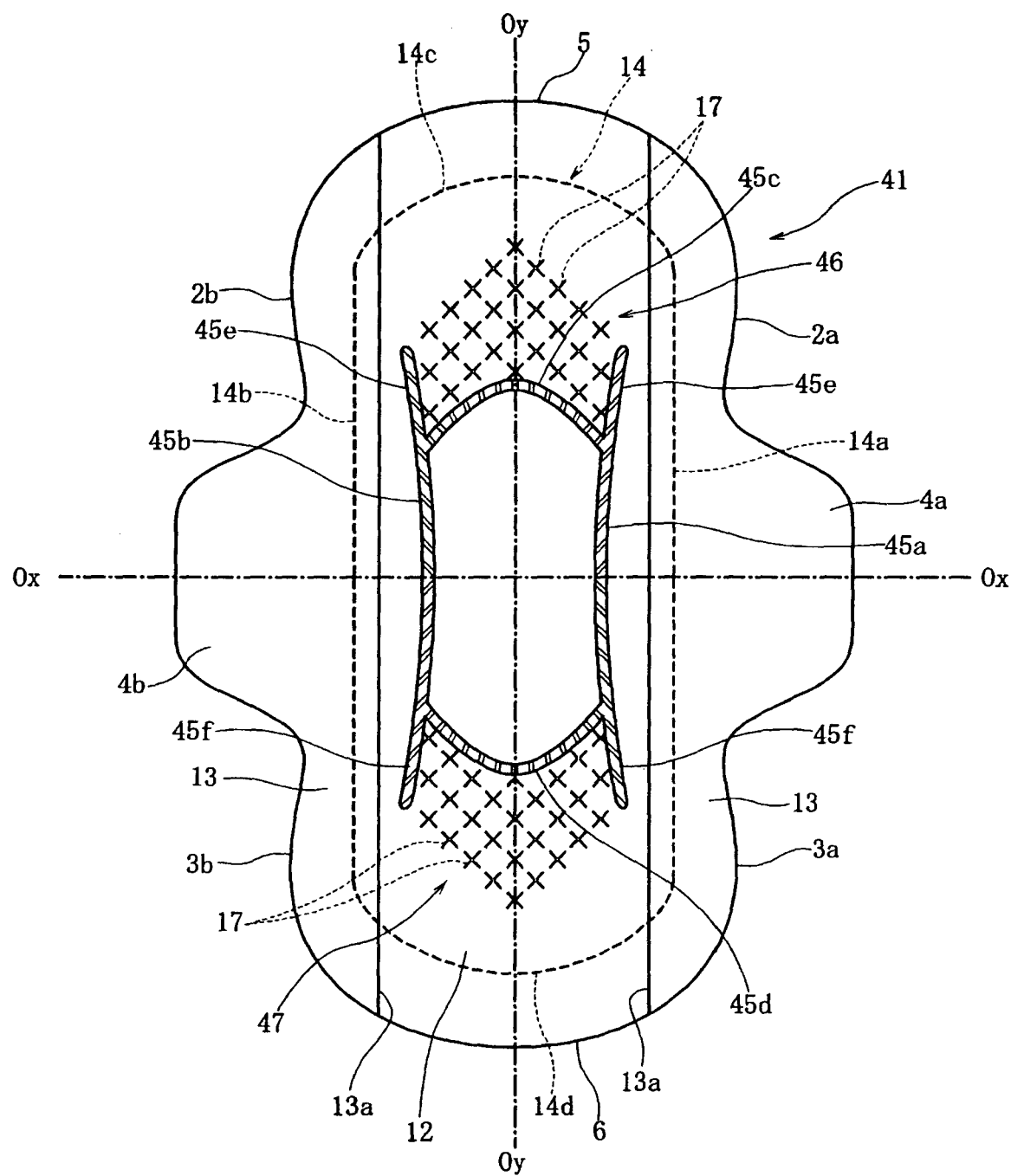
FIG. 6 is a plan view showing a modification of the first embodiment.

FIGS. 5 and 6 illustrate sanitary napkins 31 and 41, respectively, which are modifications devised from the above viewpoint.

The sanitary napkin 31 shown in FIG. 5 has the same contour as the sanitary napkin 21 shown in FIG. 3. As with the sanitary napkin 21, the sanitary napkin 31 has the right longitudinal join line 15a, the left longitudinal join line 15b, the front connecting join line 15c, the rear connecting join line 15d, the front internal connecting join line 15e, and the rear internal connecting join line 15f.

In the embodiment shown in FIG. 5, the liquid absorbent layer 14, which is an air-laid pulp or air-laid nonwoven fabric, has two low stiffness portions 14e with a number of the incisions 17 in the rear region 16b and a front region 16c, which is enclosed by the right longitudinal join line 15a, the left longitudinal join line 15b, the front connecting join line 15c, and the front internal connecting join line 15e.

On the other hand, the central region 16a, which is free of the incisions 17, has the liquid absorbent layer 14 alone or in combination with the absorbent fibrous layer 22.

In the sanitary napkin 31, since the liquid absorbent layer 14 has the low stiffness portions 14e in the front region 16c and the rear region 16b, the front region 16c and the rear region 16b are thin and reduced in bending stiffness. Accordingly, the front part of the sanitary napkin 31 can easily conform to the shape of the crotch region, while the rear part can easily conform to the cleft of the buttocks, which makes the sanitary napkin 31 less noticeable from the outside pants.

The sanitary napkin 41 shown in FIG. 6 has the same contour as the sanitary napkin 1 shown in FIG. 1. In addition, the liquid absorbent layer 14 of the sanitary napkin 41 has the same thickness and size as that of the sanitary napkin 1.

In the sanitary napkin 41 shown in FIG. 6, there are formed a right longitudinal join line 45a, which extends longitudinally on the right side of the longitudinal centerline Oy, and a left longitudinal join line 45b, which extends longitudinally on the left side of the longitudinal centerline Oy. On the front side, there is formed a front connecting join line 45c, which connects the right and left longitudinal join lines 45a, 45b. Forward of the front connecting join line 45c, front extension join lines 45e, 45e extend from the right and left longitudinal join lines 45a, 45b, respectively. The front extension join lines 45e, 45e are laterally spaced from each other. On the rear side, there is formed a rear connecting join line 45d, which connects the right and left longitudinal join lines 45a, 45b. Rearward of the rear connecting join line 45d, rear extension join lines 45f, 45f extend from the right and left longitudinal join lines 45a, 45b, respectively. The rear extension join lines 45f, 45f are laterally spaced from each other.

In a front region 46 which is enclosed on three sides by the front connecting join line 45c and the front extension join lines 45e, 45e, the liquid absorbent layer 14 has the low stiffness portion 14e with a number of the incisions 17. In a rear region 47 which is enclosed on three sides by the rear connecting join line 45d and the rear extension join lines 45f, 45*f*, likewise, the liquid absorbent layer 14 has the low stiffness portion 14*e* with a number of the incisions 17.

Also in the sanitary napkin 41, since the thin low stiffness portions 14*e* are provided in the front region 46 and the rear region 47, these parts can easily deform in accordance with the body shape of a wearer. In addition, since the front region 46 and the rear region 47 are enclosed on three sides by the join lines, the low stiffness portions 14*e* resist lateral stretching, which prevents the incisions 17 from laterally spreading and the liquid absorbent layer 14 from causing breakage from the incisions 17.

Figure 7:
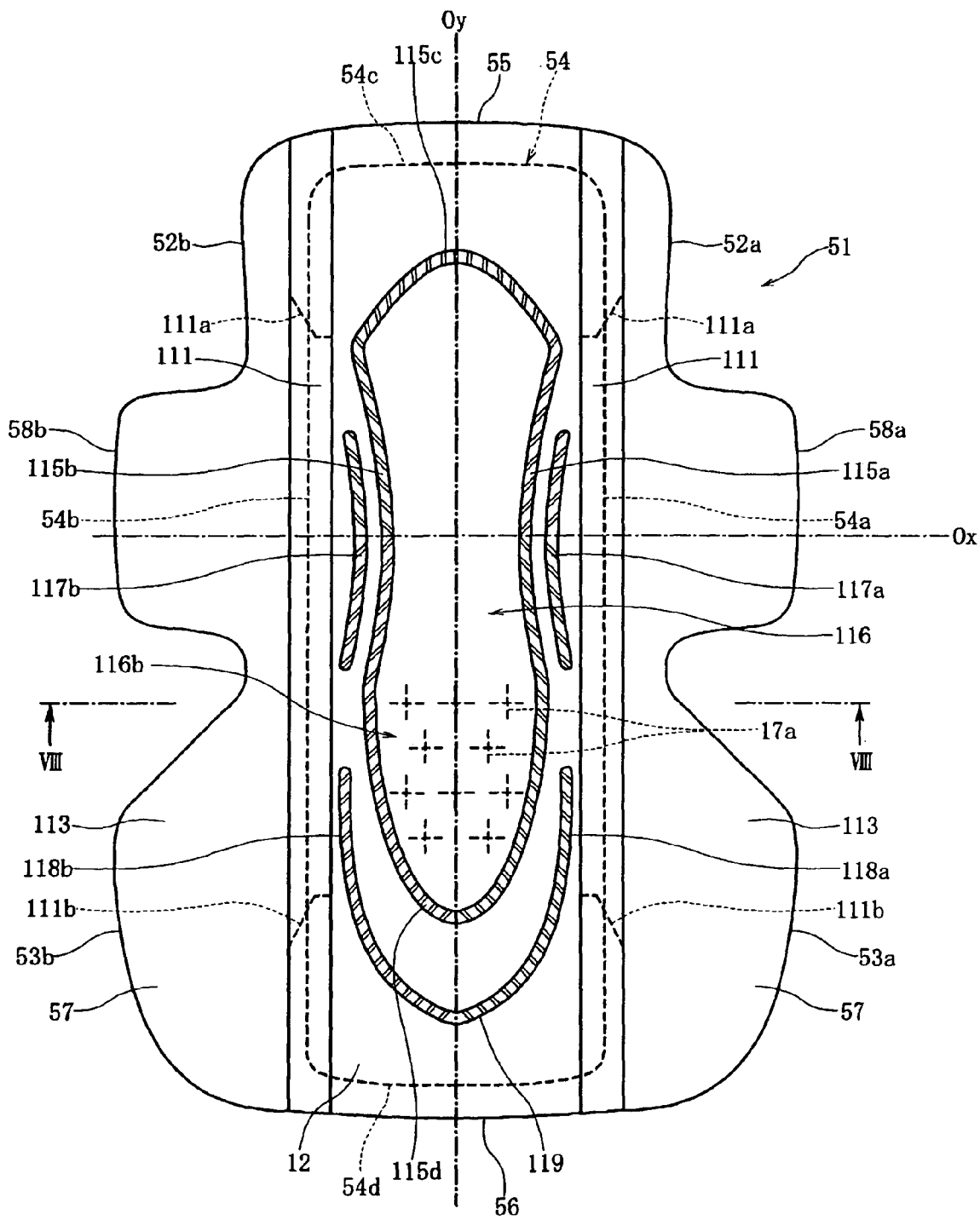
FIG. 7 is a plan view of an elongated sanitary napkin being a modification of the first embodiment.
Figure 8:
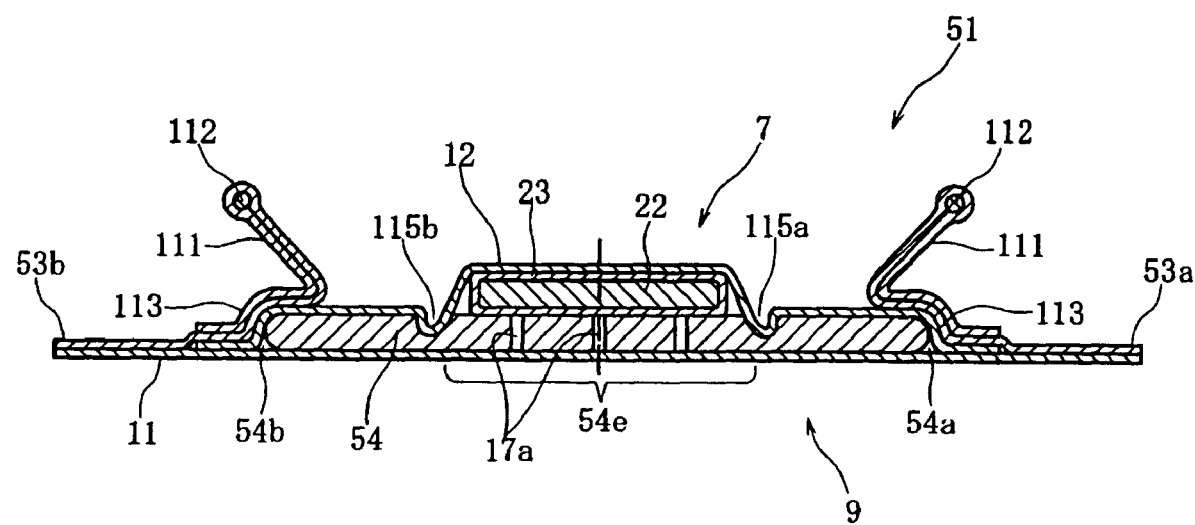
FIG. 8 is a sectional view of the sanitary napkin of FIG. 7 taken along line VIII-VIII.

FIGS. 7 and 8 illustrate a sanitary napkin 51 which is longer than the foregoing sanitary napkins 1, 21, 31, 41 and is not symmetrical about the lateral reference line Ox with the distance between the lateral reference line Ox and a rear edge 56 being greater than the distance between the lateral reference line Ox and a front edge 55. The length of the sanitary napkin 51 may be about 200 to 450 mm.

As shown in the plan view of FIG. 7, the sanitary napkin 51 has a right fold-back flap 58*a* and a left fold-back flap 58*b* behind a front right side edge 52*a* and a front left side edge 52*b*. Behind the right fold-back flap 58*a* and the left fold-back flap 58*b*, furthermore, there are provided rear flaps 57, 57 with a rear right side edge 53*a* and a rear left side edge 53*b* curved laterally outwardly.

As shown in FIG. 8, the backsheet 11, which has the same size and area as the sanitary napkin 51, is disposed on the side of the garment surface 9, the liquid-permeable topsheet 12 is exposed externally on the side of the body surface 7, and a liquid absorbent layer 54 is disposed between the backsheet 11 and the topsheet 12. The liquid absorbent layer 54 is an air-laid pulp or air-laid nonwoven fabric as is the liquid absorbent layer 14. The liquid absorbent layer 54 has a right side edge 54*a*, a left side edge 54*b*, a front edge 54*c* and a rear edge 54*d*.

FIG. 7 shows a specific pattern of join lines that are formed in the body surface 7. The pattern includes a right longitudinal join line 115*a*, a left longitudinal join line 115*b*, a front connecting join line 115*c* and a rear connecting join line 115*d*, which are connected together to define an enclosure 116.

On the right side of the right longitudinal join line 115*a*, a right external join line 117*a* is formed to extend longitudinally, and on the left side of the left longitudinal join line 115*b*, a left external join line 117*b* is formed to extend longitudinally. On the lateral reference line Ox, the distance between the right and left longitudinal join lines 115*a*, 115*b* is reduced to a minimum and the distance between the right and left external join lines 117*a*, 117*b* is also reduced to a minimum.

Between the rear flaps 57, 57, furthermore, a right rear join line 118*a* and a left rear join line 118*b* are formed on the right side of the right longitudinal join line 115*a* and on the left side of the left longitudinal join line 115*b*, respectively. Behind the rear connecting join line 115*d*, an external rear connecting join line 119 is formed to connect the right rear join line 118*a* and the left rear join line 118*b*.

The liquid absorbent layer 54 has a plurality of incisions 17*a* in a rear region 116*b* of the enclosure 116, which is located rearward of the fold-back flaps 58*a*, 58*b*. That is, the liquid absorbent layer 54 has a low stiffness portion 54*e* in the rear region 116*b*. Each incision 17*a* extends like a short straight line and crosses another incision 17*a* at a right angle. Pairs of crossing incisions 17*a* are regularly arranged. The individual incisions 17*a* extend longitudinally or laterally. Also in the enclosure 116, as with the sanitary napkin 1 shown in FIG. 1, the absorbent fibrous layer 22, which is wrapped in a hydrophilic paper material, is disposed between the liquid absorbent layer 54 and the topsheet 12, as shown in FIG. 8.

On the side of the body surface 7, as shown in FIG. 8, the sanitary napkin 51 has side sheets 113, 113 on both sides of the longitudinal centerline Oy. The side sheets 113, 113 are laid on and bonded to the backsheet 11 with a part extended to above the liquid absorbent layer 54.

The side sheets 113, 113 are folded back with elastic members 112, 112 along fold lines. The fold lines are permitted to move away from the topsheet 12 only between front and rear ends 111*a*, 111*b* shown in FIG. 7. Since the elastic members 112, 112 exert an elastic contractive force in the longitudinal direction to bring the front and rear ends 111*a*, 111*b* closer to each other, the body surface 7 of the sanitary napkin 51 can be recessed between the front and rear ends 111*a*, 111*b*, which makes the fold lines move upward away from the topsheet 12 to thereby provide leakage preventing walls (or gathers) 111, 111.

The sanitary napkin 51 may be adhered to the inner side of the crotch region of the shorts through a pressure-sensitive adhesive layer (not shown) disposed on the backsheet 11 to face the vaginal opening near the intersection of the longitudinal centerline Oy and the lateral reference line Ox. Here, the right and left fold-back flaps 58*a*, 58*b* may be folded back along the side edges of the crotch region of the shorts and adhered to the outer side of the shorts through pressure-sensitive adhesive layers (not shown).

When the sanitary napkin 51 faces the vaginal opening near the intersection of the longitudinal centerline Oy and the lateral reference line Ox, the rear region 116*b* of the enclosure 116 faces the anus or thereabout and the cleft of the buttocks with the rear edge 56 near the coccyx.

In the rear region 116*b* of the enclosure 116, the liquid absorbent layer 54 has the low stiffness portion 54*e* with a number of the incisions 17*a*. When subjected to a lifting force of the shorts, therefore, the low stiffness portion 54*e* can easily be deformed to have a reversed V-shaped cross-section with its peak directed toward the wearer's body and fit in the cleft of the buttocks near and behind the anus. Moreover, the absorbent fibrous layer 22, which is laid on the low stiffness portion 54*e*, increases the absorption capacity for menstrual blood.

Behind the enclosure 116, i.e., behind the rear connecting join line 115*d*, the thin liquid absorbent layer 54 extends without being covered with the absorbent fibrous layer 22. Also in this region behind the enclosure 116, the liquid absorbent layer 54 can easily be deformed to have a reversed V-shaped cross-section in accordance with the deformation of the low stiffness portion 54*e*, so that the rear part of the sanitary napkin 51 can easily fit in the cleft of the buttocks and the sanitary napkin 51 becomes less noticeable from the outside when wearing tight-fitting pants or the like.

Here, since the liquid absorbent layer 54 does not have the incisions 17*a* in regions beneath and near the leakage preventing walls 111 (i.e., regions between the front and rear ends 111*a*, 111*b* and outside the right and left external join lines 117*a*, 117*b*) which are under the influence of an elastic contractive force of the elastic members 112, the liquid absorbent layer 54 in these regions is effectively prevented from being twisted or undesirably deformed by the elastic contractive force of the elastic members 112.

Figure 9:
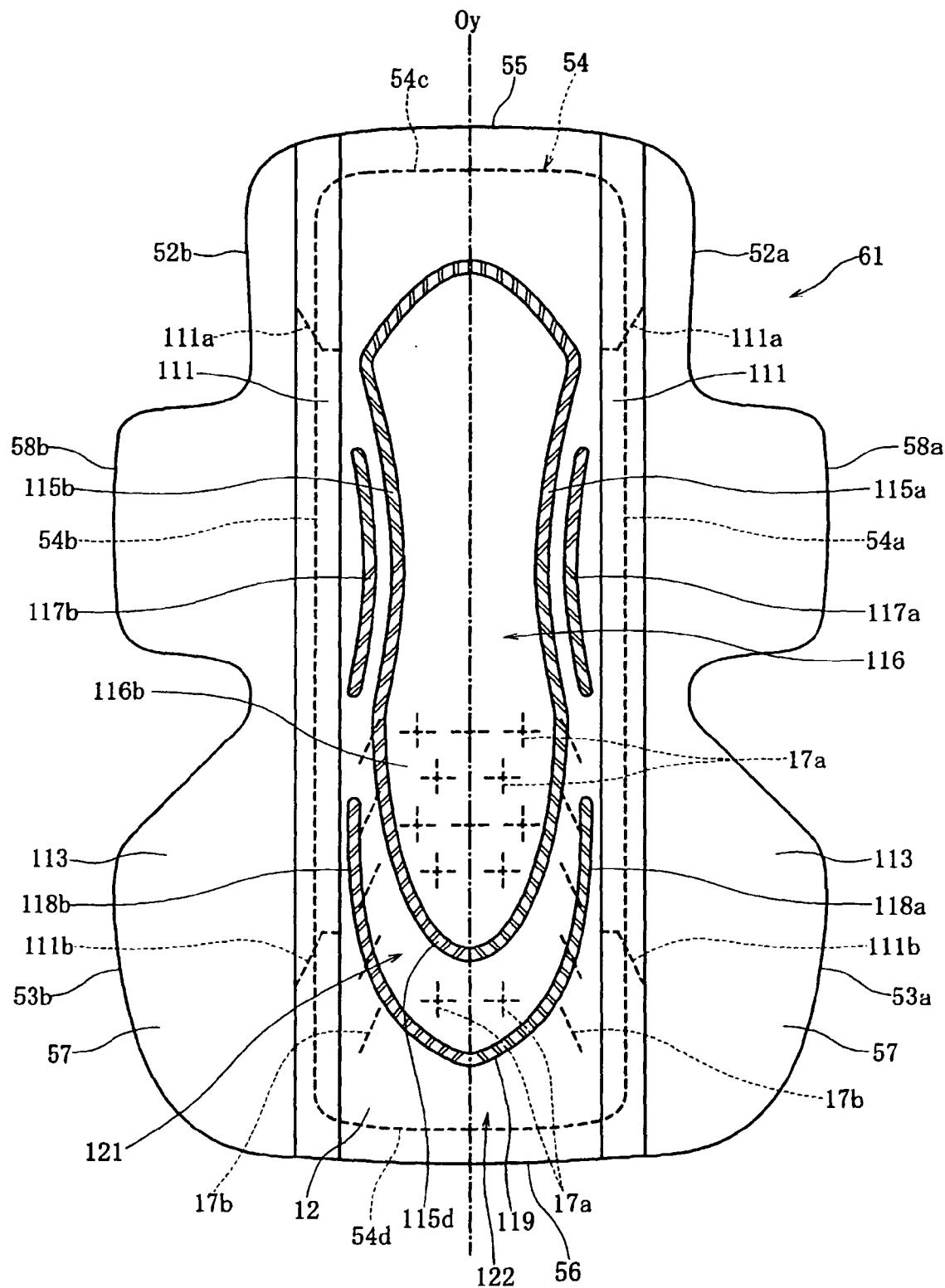
FIG. 9 is a plan view of an elongated sanitary napkin being a modification of the first embodiment.

FIG. 9 shows a sanitary napkin 61 having the same basic structure as the sanitary napkin 51 shown in FIG. 7.

In the sanitary napkin 61, the liquid absorbent layer 54 has the incisions 17*a* not only in the rear region 116*b* of the enclosure 116 but also in a second rear region 121, which is outside the right longitudinal join line 115*a*, the left longitudinal join line 115b and the rear connecting join line 115d and inside the right rear join line 118a, the left rear join line 118b and the external rear connecting join line 119. However, the arrangement density of the incisions 17a is lower in the second rear region 121 than in the rear region 116b of the enclosure 116. Therefore, the stiffness of the liquid absorbent layer 54 is higher in the second rear region 121 than in the rear region 116b of the enclosure 116.

Moreover, the liquid absorbent layer 54 has incisions 17b in a third rear region 122, which is outside the right rear join line 118a, the left rear join line 118b and the external rear connecting join line 119 and inside the rear edge 54d of the liquid absorbent layer 54. Each incision 17b extends like a short straight line and is inclined to the longitudinal centerline Oy. The arrangement density of the incisions 17b in the third rear region 122 is lower than that of the incisions 17a in the second rear region 121, so that the stiffness of the liquid absorbent layer 54 is higher in the third rear region 122 than in the second rear region 121.

In the sanitary napkin 61, since the incisions 17a are provided not only in the rear region 116b of the enclosure 116 but also in the second rear region 121 and the incisions 17b are further provided in the third rear region 122, the liquid absorbent layer 54 can easily be deformed in the rear part of the sanitary napkin 61 to fit in the cleft of the buttocks.

In the first embodiment and its modifications, the liquid absorbent layer 14, 54 is not limited to an air-laid pulp or air-laid nonwoven fabric. For example, there may be employed a deposition of pulp fibers which is wrapped in a hydrophilic paper material such as tissue and then increased in pulp fiber density by embossing or other compression forming. By forming the incisions 17, 17a, 17b in the liquid absorbent layer thus manufactured, the low stiffness portion 14e, 54e can be obtained.

Figure 10:
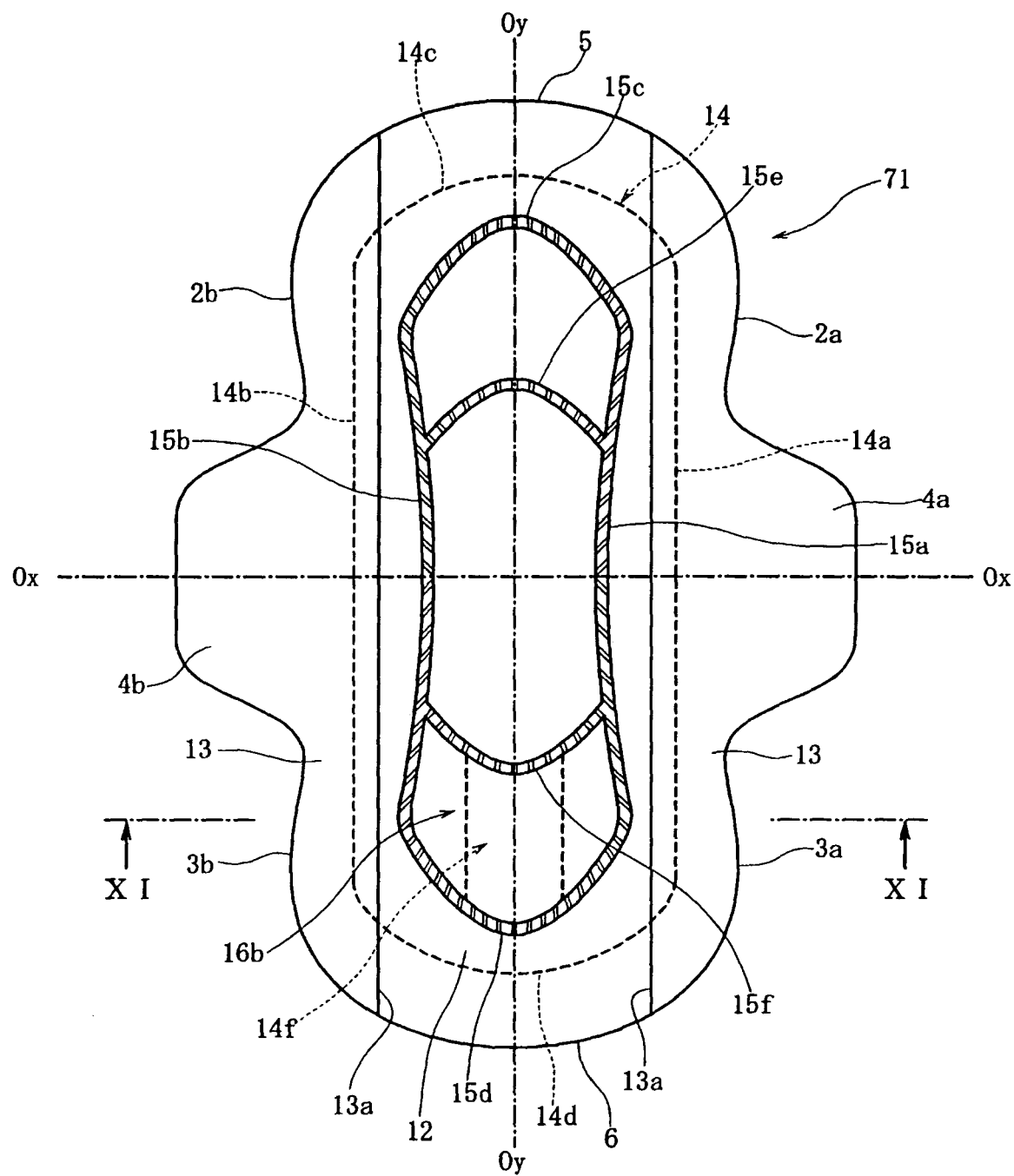
FIG. 10 is a plan view of a sanitary napkin according to a second embodiment of the present invention.
Figure 11:
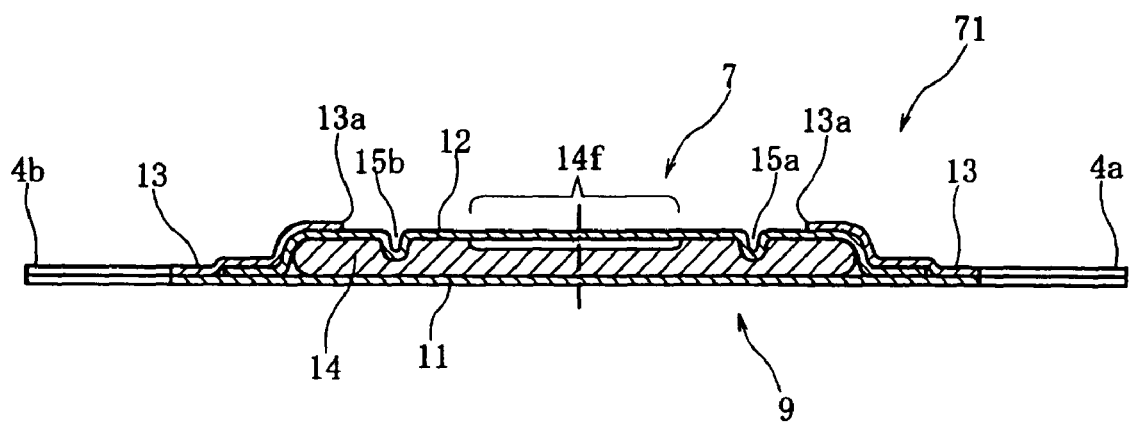
FIG. 11 is a sectional view of the sanitary napkin of FIG. 10 taken along line XI-XI.

FIG. 10 is a plan view of a sanitary napkin 71 according to a second embodiment of the present invention, and FIG. 11 is a sectional view of the sanitary napkin 71 taken along line XI-XI of FIG. 10.

The sanitary napkin 71 has the same basic construction as the sanitary napkin 1 shown in FIGS. 3 and 4.

The sanitary napkin 71 has the right longitudinal join line 15a, the left longitudinal join line 15b, the front connecting join line 15c, the rear connecting join line 15d, the front internal connecting join line 15e and the rear internal connecting join line 15f. In the rear region 16b enclosed by the right longitudinal join line 15a, the left longitudinal join line 15b, the rear connecting join line 15d and the rear internal connecting join line 15f, the liquid absorbent layer 14 has a low stiffness portion 14f in which unit weight and density are lower than in the other portions. It should be noted that although both the unit weight and the density are preferably reduced in the low stiffness portion 14f, as set forth above, it is also allowed to reduce only one of the unit weight and the density.

The low stiffness portion 14f may be formed as follows. When the liquid absorbent layer 14 is an air-laid pulp or air-laid nonwoven fabric, it may be locally stretched to form the low stiffness portion 14f. When the liquid absorbent layer 14 is a deposition of pulp fibers, on the other hand, unit weight of the pulp fiber deposition may be locally reduced to form the low stiffness portion 14f, while the other portions of the pulp fiber deposition may be compressed by embossing or other means to have a higher density and a higher stiffness.

In the low stiffness portion 14f, the unit weight of the liquid absorbent layer 14 may be in the range of 100 to 300 g/m$^2$ and the density may be in the range of 0.02 to 0.07 g/cm$^3$. In the portions other than the low stiffness portion 14f, the unit weight of the liquid absorbent layer 14 may be at least 200 g/m$^2$, preferably at least 350 g/m$^2$, while its upper limit may be about 1000 g/m$^2$. Also in the portions other than the low stiffness portion 14f, the density is preferably in the range of 0.05 to 0.2 g/cm$^3$.

Here, the difference in unit weight of the liquid absorbent layer 14 between the low stiffness portion 14f and the portions other than the low stiffness portion 14f is preferably equal to or greater than 100 g/m$^2$. On the other hand, the difference in density of the liquid absorbent layer 14 between the low stiffness portion 14f and the portions other than the low stiffness portion 14f is preferably equal to or greater than 0.02 g/cm$^3$.

As measured in the lateral direction (i.e., in a direction parallel to the lateral reference line Ox), the low stiffness portion 14f of the liquid absorbent layer 14 has a bending stiffness (Gurley stiffness) of 100 to 400 mg (0.98 to 3.92 mN) per 25.4 mm width, preferably of 150 to 350 mg (1.47 to 3.43 mN) per 25.4 mm width. In the portions other than the low stiffness portion 14f, on the other hand, the lateral bending stiffness (Gurley stiffness) of the liquid absorbent layer 14 is higher than in the low stiffness portion 14f and exceeds 400 mg (3.92 mN) per 25.4 mm width, preferably exceeds 500 mg (4.90 mN) per 25.4 mm width.

A test sample for measurement of the Gurley stiffness of the low stiffness portion 14f may be obtained by preparing a liquid absorbent layer to have the same unit weight and density as the low stiffness portion 14f, sandwiching the liquid absorbent layer between the topsheet 12 and the backsheet 11, bonding them through a hot-melt type adhesive or the like which is applied in the same manner as in the sanitary napkin 71, and then cutting the laminate into a size of 25.4 mm width and 38 mm length. A test sample for measurement of the Gurley stiffness of the portions other than the low stiffness portion 14f may likewise be obtained, wherein a liquid absorbent layer is prepared to have the same unit weight and density as the portions other than the low stiffness portion 14f.

These test samples may be tested for the Gurley stiffness using a Gurley stiffness tester (product number: 311) manufactured by YASUDA SEIKI SEISAKUSHO., LTD.

Since the low stiffness portion 14f is provided in the rear region 16b enclosed by the right longitudinal join line 15a, the left longitudinal join line 15b, the rear connecting join line 15d and the rear internal connecting join line 15f, when the shorts exert a lifting force, this region can easily be deformed toward the wearer's body to have a reversed V-shaped cross-section. In addition, since the low stiffness portion 14f is enclosed by the join lines, the topsheet 12 functions to prevent stretch of the low stiffness portion 14f. This effectively prevents twist or undesirable deformation of the liquid absorbent layer 14.

In the rear region 16b, however, at least either the topsheet 12 or the backsheet 11 may be corrugated so as to be stretchable in the lateral direction. Alternatively, at least either the topsheet 12 or the backsheet 11 may be a laterally stretchable sheet.

With this construction, the rear region 16b during wear is permitted to slightly stretch in the lateral direction for facilitating deformation in accordance with the crotch region and the cleft of the buttocks near and behind the anus. However, the elongation percentage of the topsheet 12 and the backsheet 11 in the lateral direction is limited to such an extent that the low stiffness portion 14f will not break or will not be extremely reduced in thickness.

Figure 12:
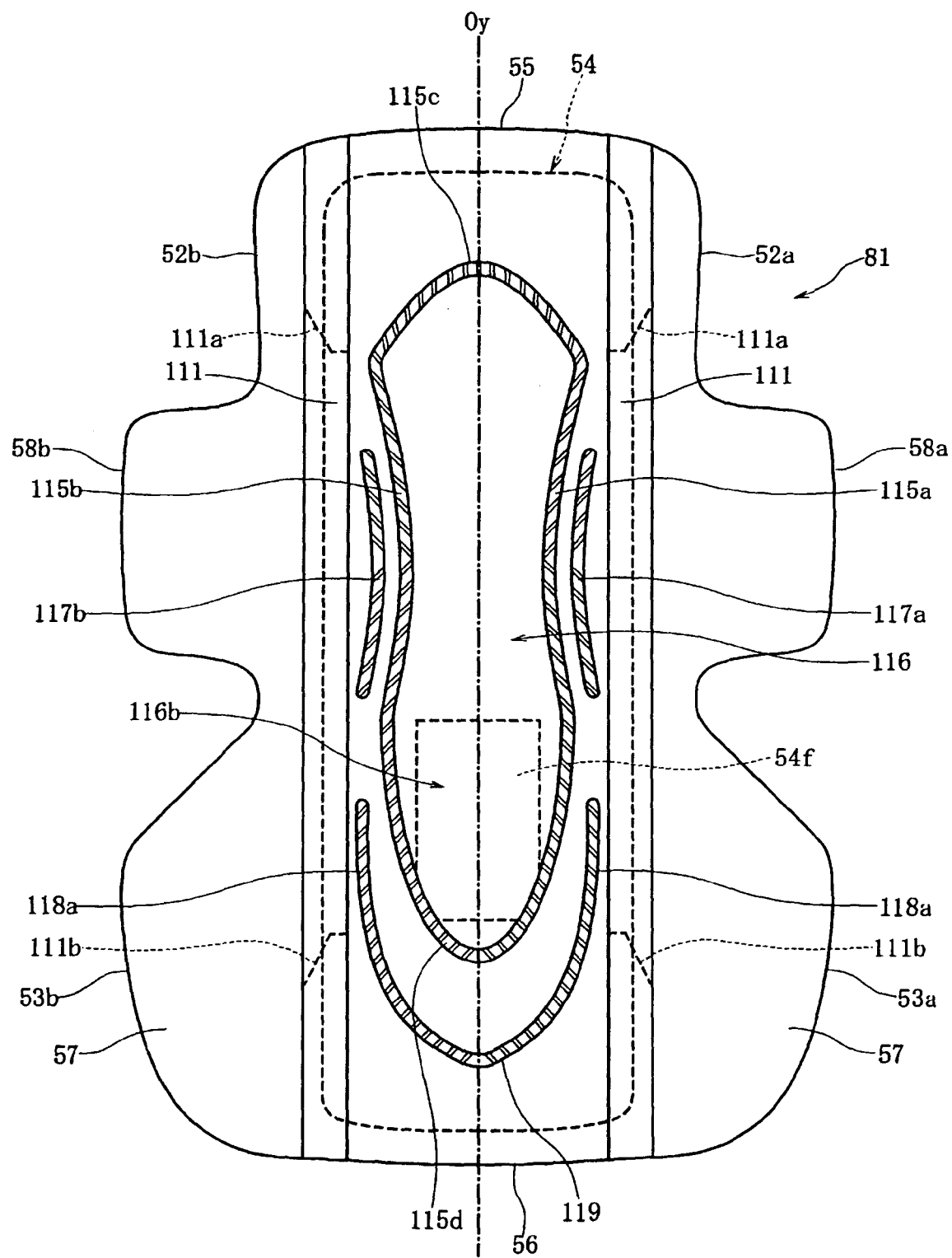
FIG. 12 is a plan view of an elongated sanitary napkin being a modification of the second embodiment.

FIG. 12 is a plan view of a sanitary napkin 81 as a modification of the second embodiment. The sanitary napkin 81 shown in FIG. 12 has the same basic structure and shape as the sanitary napkin 51 shown in FIG. 7. Also in the sanitary napkin 81, the join lines are arranged in the same pattern as shown in FIG. 7.

In the rear region 116b of the enclosure 116 enclosed by the right longitudinal join line 115a, the left longitudinal join line 115b, the front connecting join line 115c and the rear connecting join line 115d, the liquid absorbent layer 54 has a low stiffness portion 54f. The low stiffness portion 54f is formed in the same manner as the low stiffness portion 14f of the sanitary napkin 71 shown in FIG. 10 and therefore has the same effect as the sanitary napkin 51 shown in FIG. 7.

Figure 13:
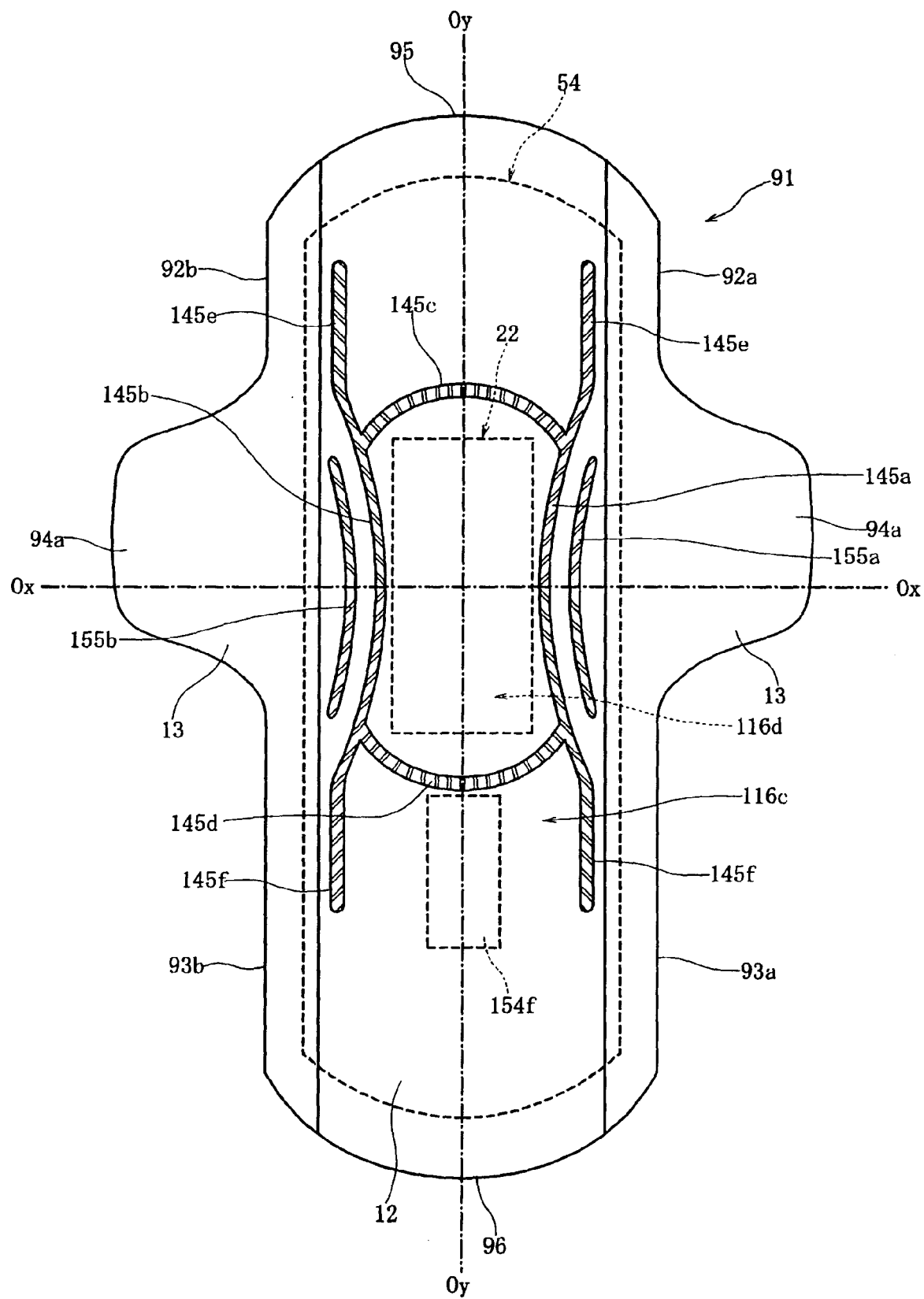
FIG. 13 is a plan view of an elongated sanitary napkin being a modification of the second embodiment.

FIG. 13 shows a sanitary napkin 91, which is so elongated as to have a rear edge 96 near the coccyx when the intersection of the longitudinal centerline Oy and the lateral reference line Ox is in contact with the vaginal opening, like the sanitary napkin 51 shown in FIG. 7 and the sanitary napkin 81 shown in FIG. 12.

As shown in the plan view of FIG. 13, the sanitary napkin 91 has a right fold-back flap 94a and a left fold-back flap 94b behind a front right side edge 92a and a front left side edge 92b, respectively. Behind the right fold-back flap 94a and the left fold-back flap 94b, a rear right side edge 93a and a rear left side edge 93b extend straight in the longitudinal direction without providing the rear flaps 57 shown in FIGS. 7 and 12. On the front side, the sanitary napkin 91 has a front edge 95.

The sanitary napkin 91 includes the backsheet 11, the topsheet 12, the side sheets 13 and the liquid absorbent layer 54.

In an enclosure 116d defined by a right longitudinal join line 145a, a left longitudinal join line 145b, a front connecting join line 145c and a rear connecting join line 145d, the absorbent fibrous layer 22 is laid on the liquid absorbent layer 54.

Forward of the front connecting join line 145c, front extension join lines 145e, 145e extend from the right and left longitudinal join lines 145a, 145b, respectively. Rearward of the rear connecting join line 145d, rear extension join lines 145f, 145f extend from the right and left longitudinal join lines 145a, 145b, respectively.

In a rear region 116c enclosed on three sides by the rear connecting join line 145d and the rear extension join lines 145f, 145f, the liquid absorbent layer 54 has a low stiffness portion 154f. The low stiffness portion 154f is formed in the same manner as the low stiffness portion 14f shown in FIG. 10 and the low stiffness portion 54f shown in FIG. 12.

As described hereinabove, the liquid absorbent layer 54 is a thin absorbent layer such as an air-laid pulp, air-laid nonwoven fabric, or compressed pulp fiber deposition, and because the liquid absorbent layer 54 has the low stiffness portion 154f, the rear region 116c behind the rear connecting join line 145d can easily be deformed toward the wearer's body. Hence, the sanitary napkin 91 has the same effects as the first embodiment and its modifications. In addition, since the low stiffness portion 154f is enclosed on three sides by the join lines and covered with the topsheet 12 which is joined to the liquid absorbent layer 54 at the join lines, the low stiffness portion 154f is prevented from stretching or twisting.

FIGS. 14(A) to 14(F) illustrate various patterns of incisions which may be formed in the liquid absorbent layer 14, 54.

Figure 14:
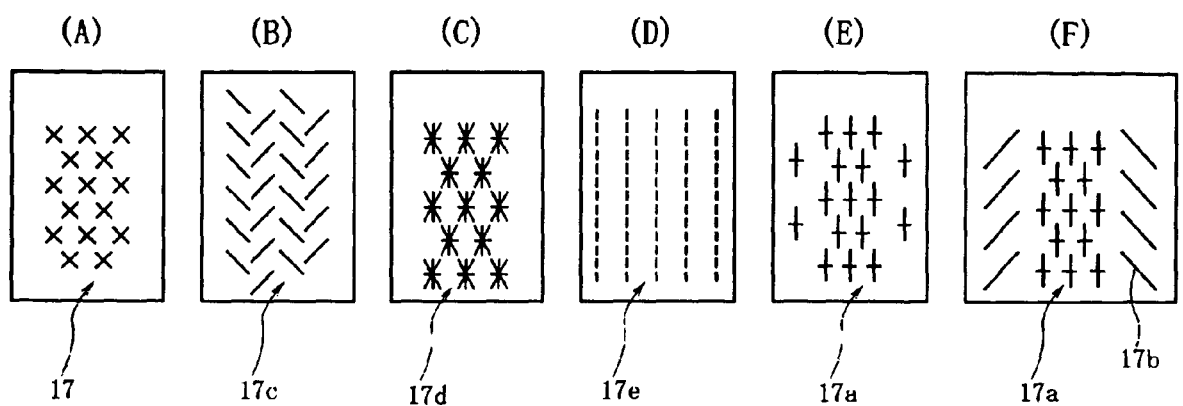
FIGS. 14(A) to 14(F) are plan views showing various patterns of incisions.

FIG. 14(A) shows a pattern of the incisions 17, wherein each short straight line-like incision 17, which is inclined at an angle of 45 degrees to both the longitudinal direction and the lateral direction, crosses another incision 17 at a right angle. FIG. 14(E) shows a pattern of the incisions 17a, wherein each short straight line-like incision 17a, which extends in either the longitudinal direction or the lateral direction, crosses another incision 17a at a right angle. FIG. 14(F) shows a pattern of the incisions 17a in combination with the incisions 17b, wherein each short straight line-like incision 17b is inclined to the longitudinal direction.

FIG. 14(B) shows a herringbone pattern of short straight line-like incisions 17c, FIG. 14(C) shows a pattern of short straight line-like incisions 17d, wherein four incisions 17d cross each other to form a unit, and FIG. 14(D) shows a pattern of incisions 17e each extending like a straight dotted line in the longitudinal direction.

It should be noted that the incision may be a small opening of a circular or oval shape, without limited to such a short straight line or a dotted line.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but should be understood to include all possible embodiments which can be embodied within a scope encompassed and equivalent thereof with respect to the feature set out in the appended claims.

What is claimed is:

1. A sanitary napkin comprising:
   a liquid absorbent layer and a liquid-permeable topsheet covering a body surface of the liquid absorbent layer, the topsheet being joined to the liquid absorbent layer in a specific pattern;
   wherein the pattern includes longitudinal join lines which extend longitudinally and are laterally spaced from each other and connecting join lines which connect the longitudinal join lines to define a continuous border defining an elongated enclosed region, and wherein the liquid absorbent layer has a thickness of 1.5 to 5 mm, and
   wherein said enclosed region of the absorbent layer comprises a plurality of incisions through the absorbent layer, and wherein said plurality of incisions are configured so that the portion of the absorbent layer inside the enclosed region has a lower stiffness than the portion of the absorbent layer outside the enclosed region.

2. The sanitary napkin of claim 1, wherein the liquid absorbent layer is an air-laid pulp made of pulp fibers, the pulp fibers being deposited by an air-laid process, pressed, and bonded together through a binder between the pulp fibers.

3. The sanitary napkin of claim 2, wherein the liquid absorbent layer is an air-laid nonwoven fabric made of pulp fibers and thermoplastic synthetic resin fibers, the pulp fibers and the thermoplastic synthetic resin fibers being deposited by an air-laid process, pressed, and bonded together through a binder between the fibers.

4. The sanitary napkin of claim 1, wherein the liquid absorbent layer is an air-laid nonwoven fabric made of pulp fibers and thermoplastic synthetic resin fibers, the pulp fibers and the thermoplastic synthetic resin fibers being deposited by an air-laid process, heated under pressure, and bonded together by fusion of the thermoplastic synthetic fibers.

5. The sanitary napkin of claim 1, wherein the liquid absorbent layer is an air-laid pulp.

6. The sanitary napkin of claim 1, wherein the liquid absorbent layer is formed by compressing a fiber deposition including pulp fibers.

7. The sanitary napkin of claim 1, wherein each incision crosses another incision at a right angle.

8. The sanitary napkin of claim 7, wherein each paired incision is inclined at an angle of 45° from the centerline of the sanitary napkin.

9. The sanitary napkin of claim 1, wherein said liquid absorbent layer has a density ranging from 0.05 to 0.2 g/cm³.

10. A sanitary napkin comprising:
a liquid absorbent layer having a top surface and a bottom surface; and
a liquid-permeable topsheet covering a body surface of the liquid absorbent layer, wherein the topsheet is joined to the liquid absorbent layer in a specific pattern including:
longitudinal join lines which extend longitudinally from a centerline of the sanitary napkin and are laterally spaced from each other each between the centerline and an edge of the liquid absorbent layer, and
connecting join lines which connect the longitudinal join lines to define a continuous border defining an elongated enclosed region,
wherein:
the liquid absorbent layer (i) has a plurality of incisions covered by the topsheet, which pass through from the top surface of the absorbent layer to the bottom surface of the absorbent layer, thereby providing a low stiffness portion in the elongated enclosed region, the liquid absorbent layer having a lower stiffness in the low stiffness portion than in portions outside the longitudinal join lines,
(ii) has a plurality of incisions regularly arranged in pairs in which each incision crosses another and each of the plurality of incisions pierces the liquid absorbent layer, the plurality of incisions being confined to and distributed over the elongated enclosed region, (iii) comprises fibers pressed into a sheet and bonded together with a binder or through fusion of said fibers, (iv) has a thickness ranging from 0.5 to 5 mm, and (v) has a unit weight ranging from 70 to 300 g/m².

11. The sanitary napkin of claim 10, wherein said liquid absorbent layer has a density ranging from 0.05 to 0.2 g/cm³.

12. A sanitary napkin comprising:
a liquid absorbent layer having a top surface and a bottom surface; and
a liquid-permeable topsheet covering a body surface of the liquid absorbent layer, wherein the topsheet is joined to the liquid absorbent layer along a continuous join line defining an elongated enclosed region, said continuous join line comprising:
longitudinal join lines which extend longitudinally from a centerline of the sanitary napkin and are laterally spaced from each other each between the centerline and an edge of the liquid absorbent layer,
front and rear connecting join lines which are respectively positioned between a lateral center line of the sanitary napkin and front and rear edges of the sanitary napkin, the front and rear connecting join lines extending laterally to connect the longitudinal join lines, wherein said topsheet is also joined to said liquid absorbent layer along
front and rear internal connecting join lines which are respectively positioned between the lateral center line and the front and rear connecting join lines,
wherein:
the liquid absorbent layer (i) has a first low stiffness portion in a first area delimited by the longitudinal join lines, the front connecting join line and the front internal connecting join line,
(ii) has a second low stiffness portion in a second area delimited by the longitudinal join lines, the rear connecting join line and the rear internal connecting join line,
(iii) has a lower stiffness in each of the first and second low stiffness portions than in portions of the liquid absorbent layer outside of the first and second areas,
(iv) has a plurality of incisions covered by the topsheet, which pass through from the top surface of the absorbent layer to the bottom surface of the absorbent layer, and regularly arranged in pairs in which the paired incisions cross one another and each of the plurality of incisions pierces the liquid absorbent layer, (v) comprises fibers pressed into a sheet and bonded together with a binder or through fusion of said fibers, (vi) has a thickness ranging from 0.5 to 5 mm, and (vii) has a unit weight ranging from 70 to 300 g/m², and
the plurality of incisions are confined to and distributed over the first and second areas.

13. The sanitary napkin of claim 12, wherein said liquid absorbent layer has a density ranging from 0.05 to 0.2 g/cm³.

* * * * *